US00PP25324P2

(12) United States Plant Patent
Takeuchi

(10) Patent No.: US PP25,324 P2
(45) Date of Patent: Mar. 3, 2015

(54) ***ANTIRRHINUM* PLANT NAMED 'KEIANPINETUM'**

(50) Latin Name: *Antirrhinum hybrida*
Varietal Denomination: Keianpinetum

(71) Applicant: Shunsuke Takeuchi, Kozaki-Machi (JP)

(72) Inventor: Shunsuke Takeuchi, Kozaki-Machi (JP)

(73) Assignee: Keisei Rose Nurseries, Inc., Tokyo (JP)

( * ) Notice: Subject to any disclaimer, the term of this patent is extended or adjusted under 35 U.S.C. 154(b) by 127 days.

(21) Appl. No.: 13/815,650

(22) Filed: Mar. 13, 2013

(51) Int. Cl.
*A01H 5/00* (2006.01)

(52) U.S. Cl.
USPC ..... Plt./322

(58) Field of Classification Search
CPC ..... A01H 5/02
USPC ..... Plt./322
See application file for complete search history.

*Primary Examiner* — June Hwu
(74) *Attorney, Agent, or Firm* — C. A. Whealy

(57) ABSTRACT

A new and distinct cultivar of *Antirrhinum* plant named 'Keianpinetum', characterized by its semi-upright and mounded plant habit; vigorous growth habit; freely branching habit and short internodes; dense and bushy plant form; numerous bright yellow-colored flowers; long flowering period; and good garden performance.

2 Drawing Sheets

Botanical designation: *Antirrhinum hybrida.*
Cultivar denomination: 'KEIANPINETUM'.

BACKGROUND OF THE INVENTION

The present invention relates to a new and distinct cultivar of *Antirrhinum* plant, botanically known as *Antirrhinum hybrida* and hereinafter referred to by the name 'Keianpinetum'.

The new *Antirrhinum* plant is a product of a planned breeding program conducted by the Inventor in Katori-shi, Chiba-ken, Japan. The objective of the breeding program is to create new compact and freely flowering potted *Antirrhinum* plants with unique and attractive flower coloration.

The new *Antirrhinum* plant originated from a cross-pollination in Katori-shi, Chiba-ken, Japan in October, 2008 of *Antirrhinum hybrida* 'Keianmilkwam', disclosed in U.S. Plant Pat. No. 19,087, as the female, or seed, parent with a proprietary selection of *Antirrhinum hybrida* identified as code number J05-1M, not patented, as the male, or pollen, parent. The new *Antirrhinum* plant was discovered and selected by the Inventor as a single flowering plant from within the progeny of the stated cross-pollination in a controlled environment in Katori-shi, Chiba-ken, Japan in April, 2009.

Asexual reproduction of the new *Antirrhinum* plant by vegetative terminal cuttings in a controlled environment in Katori-shi, Chiba-ken, Japan since April, 2009 has shown that the unique features of this new *Antirrhinum* plant are stable and reproduced true to type in successive generations.

SUMMARY OF THE INVENTION

Plants of the new *Antirrhinum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Keianpinetum'. These characteristics in combination distinguish 'Keianpinetum' as a new and distinct *Antirrhinum* plant:

1. Semi-upright and mounded plant habit.
2. Vigorous growth habit.
3. Freely branching habit and short internodes; dense and bushy plant form.
4. Numerous bright yellow-colored flowers.
5. Long flowering period.
6. Good garden performance.

Plants of the new *Antirrhinum* differ from plants of the female parent, 'Keianmilkwam', primarily in flower color as plants of 'Keianmilkwam' have white and yellow bi-colored flowers.

Plants of the new *Antirrhinum* differ from plants of the male parent selection primarily in plant size as plants of the new *Antirrhinum* are taller than plants of the male parent selection. In addition, plants of the new *Antirrhinum* and the male parent selection differ in leaf and flower color as plants of the male parent selection have variegated leaves and orange-colored flowers.

Plants of the new *Antirrhinum* can be compared to plants of *Antirrhinum hybrida* 'Keiananzurem', disclosed in U.S. Plant Pat. No. 19,084. In side-by-side comparisons conducted in Katori-shi, Chiba-ken, Japan, plants of the new *Antirrhinum* and 'Keiananzurem' differed in the following characteristics:

1. Plants of the new *Antirrhinum* had longer leaves than plants of 'Keiananzurem'.
2. Plants of the new *Antirrhinum* had longer flowers than plants of 'Keiananzurem'.
3. Plants of the new *Antirrhinum* and 'Keiananzurem' differed in flower color as plants of 'Keiananzurem' had soft orange and yellow bi-colored flowers.
4. Plants of the new *Antirrhinum* had longer pedicels than plants of 'Keiananzurem'.

BRIEF DESCRIPTION OF THE PHOTOGRAPHS

The accompanying colored photographs illustrate the overall appearance of the new *Antirrhinum* plant showing the colors as true as it is reasonably possible to obtain in colored reproductions of this type. Colors in the photographs may differ slightly from the color values cited in the detailed botanical description which accurately describe the colors of the new *Antirrhinum* plant.

The photograph on the first sheet comprises a side perspective view of a typical flowering plant of 'Keianpinetum' grown in a container.

The photograph on the second sheet is a close-up view of a typical inflorescence of 'Keianpinetum'.

DETAILED BOTANICAL DESCRIPTION

The aforementioned photographs and following observations, measurements and values describe plants grown during the winter in 21-cm containers in a glass-covered greenhouse in Katori-shi, Chiba-ken, Japan and under cultural practices typical of commercial *Antirrhinum* production. During the production of the plants, day temperatures averaged 15° C. and night temperatures averaged 5° C. Plants were six months old when the photographs and description were taken. In the following description, color references are made to The Royal Horticultural Society Colour Chart, 2007 Edition, except where general terms of ordinary dictionary significance are used.

Botanical classification: *Antirrhinum hybrida* 'Keianpinetum'.

Parentage:

*Female, or seed, parent.*—*Antirrhinum hybrida* 'Keianmilkwam', disclosed in U.S. Plant Pat. No. 19,087.

*Male, or pollen, parent.*—Proprietary selection of *Antirrhinum hybrida* identified as code number J05-1M, not patented.

Propagation:

*Type.*—By vegetative terminal cuttings.

*Time to initiate roots, summer.*—About two weeks at 25° C.

*Time to initiate roots, winter.*—About three weeks at 10° C.

*Time to produce a rooted young plant, summer.*—About four weeks at 25° C.

*Time to produce a rooted young plant, winter.*—About five weeks at 15° C.

*Root description.*—Fine, fibrous; white in color.

*Rooting habit.*—Freely branching; dense.

Plant description:

*Plant and growth habit.*—Semi-upright and mounded plant habit; broad inverted triangle; freely branching habit with short internodes; dense and bushy plant form; vigorous growth habit.

*Plant height.*—About 29 cm.

*Plant width (spread).*—About 50 cm.

*Lateral branches.*—Length: About 28 cm. Diameter: About 2.5 mm. Internode length: About 1.8 cm. Strength: Moderately strong. Texture: Pubescent. Color: Close to 143C.

Foliage description:

*Arrangement.*—Alternate, simple; sessile

*Length.*—About 4.7 cm.

*Width.*—About 1.4 cm.

*Shape.*—Elliptic.

*Apex.*—Obtuse.

*Base.*—Obtuse.

*Margin.*—Entire.

*Texture, upper and lower surfaces.*—Pubescent; slightly viscid.

*Venation pattern.*—Pinnate; reticulate.

*Color.*—Developing leaves, upper surface: Close to 143A. Developing leaves, lower surface: Close to 143B. Fully expanded leaves, upper surface: Close to 137B; venation, close to 137B. Fully expanded leaves, lower surface: Close to 137D; venation, close to 137D.

Flower description:

*Flower type and flowering habit.*—Single bi-labiate flowers arranged in terminal racemes; flowers face mostly outwardly; freely flowering habit with about 10 to 15 flowers per inflorescence and numerous flowers developing per plant.

*Fragrance.*—Slightly sweet.

*Natural flowering season.*—Continuously flowering throughout the spring and summer into the autumn in Japan.

*Postproduction longevity.*—Flowers last about five days on the plant; flowers not persistent.

*Flower buds.*—Height: About 2.2 cm. Diameter: About 1 cm. Shape: Oval. Color: Close to 179C.

*Inflorescence height.*—About 8 cm.

*Inflorescence diameter.*—About 8 cm.

*Flower diameter.*—About 2.7 cm.

*Flower depth (height).*—About 4.7 cm.

*Petals.*—Quantity and arrangement: Upper lip, two-lobed; lower lip, three-lobed; petals fused at the base. Length, upper lip: About 3.1 cm. Width, upper lip: About 3.6 cm. Length, lower lip: About 2.3 cm. Width, lower lip: About 3.3 cm. Apex, upper and lower lips: Rounded. Margin, upper and lower lips: Entire; weakly undulate. Texture, upper and lower lips, upper and lower surfaces: Smooth, glabrous; satiny. Color, upper and lower lips: When opening, upper surface: Close to 9A; towards the margins, close to 180D. When opening, lower surface: Close to 27C; towards the margins, close to 36C. Fully opened, upper surface: Close to 7C; towards the margins, close to 9C; with development, color becoming closer to 8C and towards the margins, close to 8D. Fully opened, lower surface: Close to 18D; towards the margins, close to 36D.

*Sepals.*—Quantity and arrangement: Five in a single whorl. Length: About 8 mm. Width: About 4 mm. Shape: Narrowly elliptic. Apex: Broadly acute. Margin: Entire. Texture, upper and lower surfaces: Pubescent. Color, upper and lower surfaces: Close to 143C.

*Pedicels.*—Length: About 7 mm. Diameter: About 1 mm. Strength: Strong. Texture: Pubescent. Color: Close to 144D.

*Reproductive organs.*—Stamens: Quantity per flower: Typically four. Anther size: About 2.5 mm by 3 mm. Anther shape: Elliptical. Anther color: Close to 17C. Pollen amount: Moderate. Pollen color: Close to 17C. Pistils: Quantity per flower: One. Pistil length: About 2.5 cm. Stigma shape: Elliptical. Stigma color: Close to 144C. Style length: About 2 cm. Style color: Close to 145D. Ovary color: Close to 145D.

*Seeds.*—Shape: Spherical. Length: About 0.5 mm. Diameter: About 0.5 mm. Color: Close to 200A.

Disease & pest resistance: Plants of the new *Antirrhinum* have not been noted to be resistant to pathogens and pests common to *Antirrhinum*.

Garden performance: Plants of the new *Antirrhinum* have been observed to have excellent garden performance and tolerate rain, wind and temperatures ranging from about −5° C. to about 35° C.

It is claimed:

1. A new and distinct *Antirrhinum* plant named 'Keianpinetum' as illustrated and described.

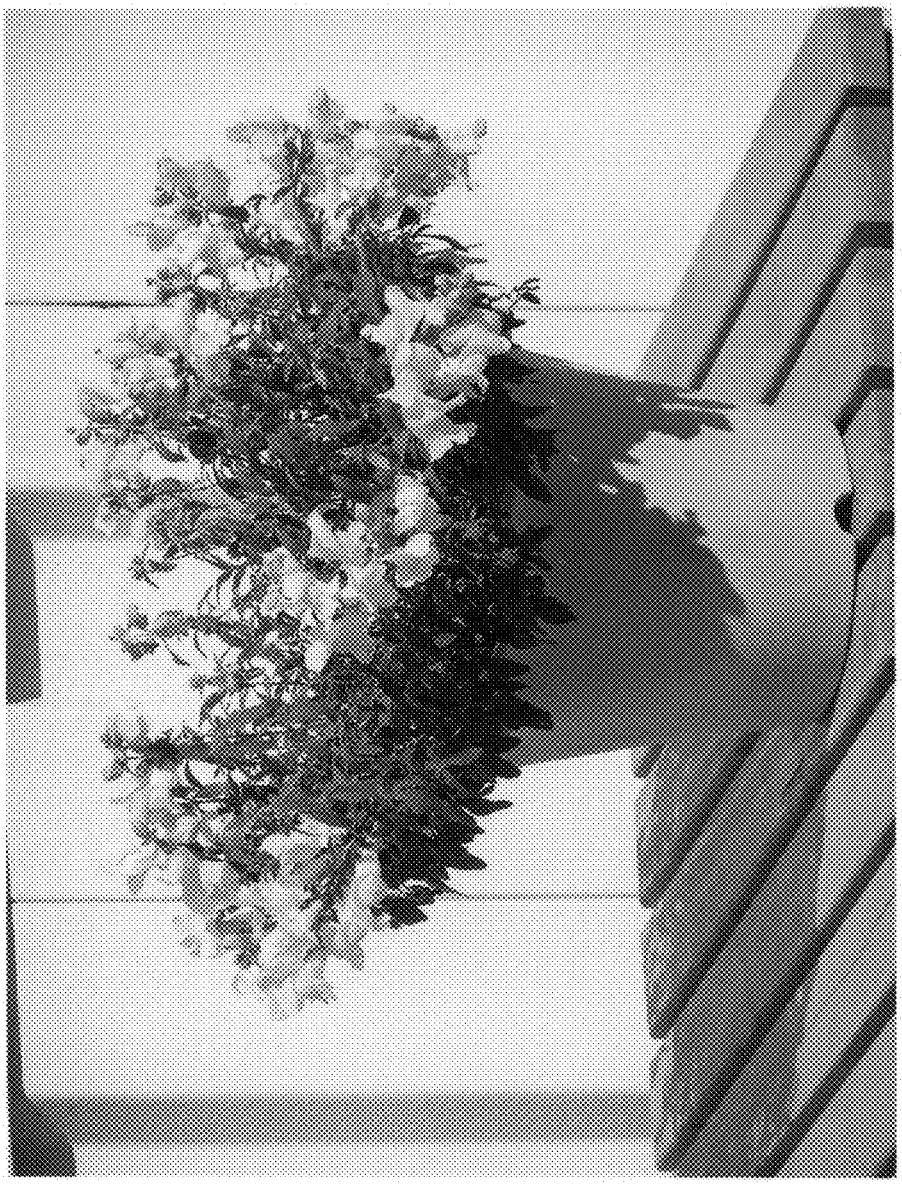

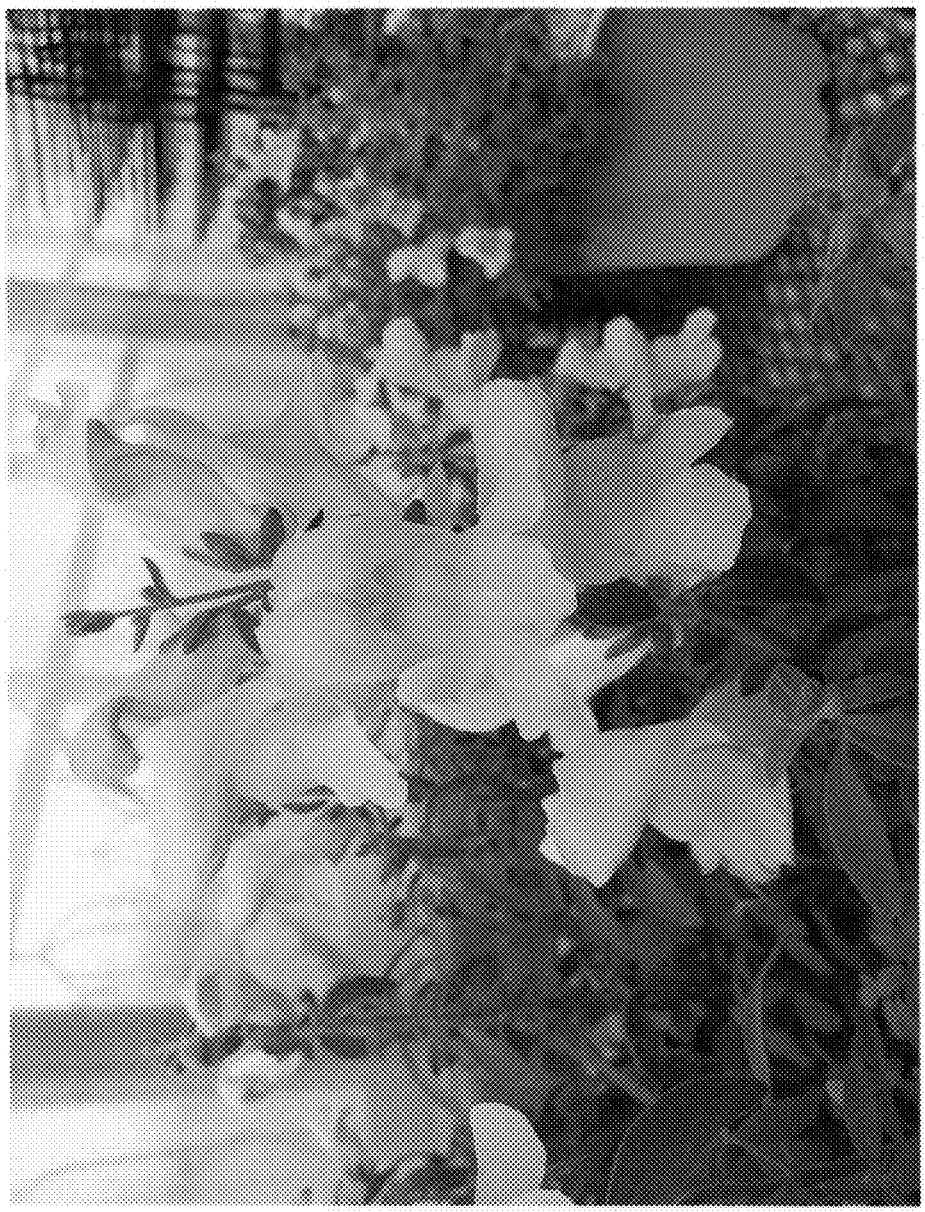

* * * * *